(12) United States Patent
Bonnin et al.

(10) Patent No.: US 6,183,519 B1
(45) Date of Patent: Feb. 6, 2001

(54) ANKLE PROSTHESIS

(75) Inventors: Michel Bonnin, Francheville; Jean-Alain Colombier, Balma; Thierry Judet, Ville d'Avray; Alain Tornier, Saint-Ismier, all of (FR)

(73) Assignee: Tornier SA, Saint Ismier (FR)

( * ) Notice: Under 35 U.S.C. 154(b), the term of this patent shall be extended for 0 days.

(21) Appl. No.: 09/036,682

(22) Filed: Mar. 9, 1998

(30) Foreign Application Priority Data

Mar. 10, 1997 (FR) .................................................. 97 03040

(51) Int. Cl.$^7$ ....................................................... A61F 2/42
(52) U.S. Cl. .................................... 623/21.18; 623/21.11
(58) Field of Search ........................... 623/21, 18, 21.11, 623/21.18

(56) References Cited

U.S. PATENT DOCUMENTS

| | | |
|---|---|---|
| 3,896,502 | 7/1975 | Lennox . |
| 3,975,778 | 8/1976 | Newton, III . |
| 4,069,518 * | 1/1978 | Groth, Jr. et al. ...................... 623/21 |
| 4,156,944 * | 6/1979 | Schreiber et al. ..................... 623/21 |
| 4,232,404 | 11/1980 | Samuelson et al. . |
| 4,792,340 * | 12/1988 | Aule et al. .............................. 623/21 |
| 5,766,259 * | 6/1998 | Sammarco .............................. 623/21 |
| 5,824,106 * | 10/1998 | Fournol ................................... 623/21 |

FOREIGN PATENT DOCUMENTS

| | | |
|---|---|---|
| 2401481 | 7/1974 | (DE) . |
| 2370465 | 6/1978 | (FR) . |
| 2684291 | 6/1993 | (FR) . |
| 2700462 | 7/1994 | (FR) . |
| 2724108 | 3/1996 | (FR) . |

* cited by examiner

*Primary Examiner*—David H. Willse
*Assistant Examiner*—Suzette J. Jackson
(74) *Attorney, Agent, or Firm*—Dowell & Dowell, P.C.

(57) ABSTRACT

An ankle prosthesis, comprising a tibial element and an talar element (30), each provided with anchoring means on the lower extremity of a tibia and on the astragalus, respectively, and each delimiting an articular surface, both articular surfaces being shaped in order to interact as a whole and to provide a relative movement between the two tibial and talar elements around at last one axis. It is especially characterized by the fact that, taking as reference direction the direction of the axis of the tibia on which it is intended to anchor the tibial element, seen in projection on a plane approximately perpendicular to this reference direction, the articular surfaces are curved with a concavity towards the inside of the foot onto which is to be anchored the talar element.

15 Claims, 2 Drawing Sheets

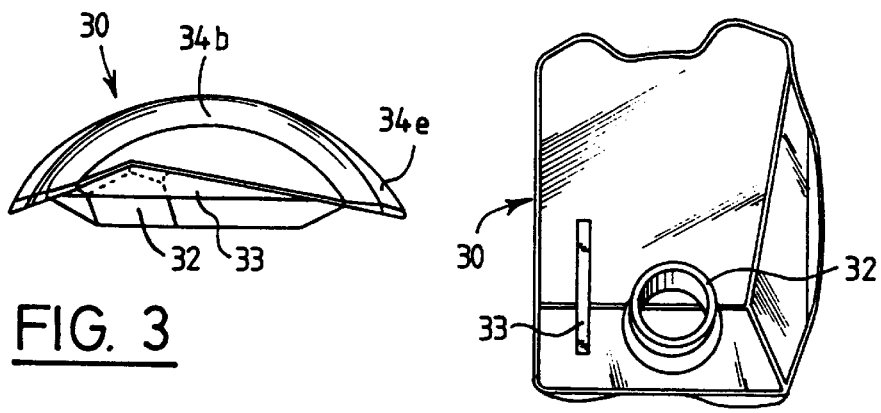
FIG. 3
FIG. 4
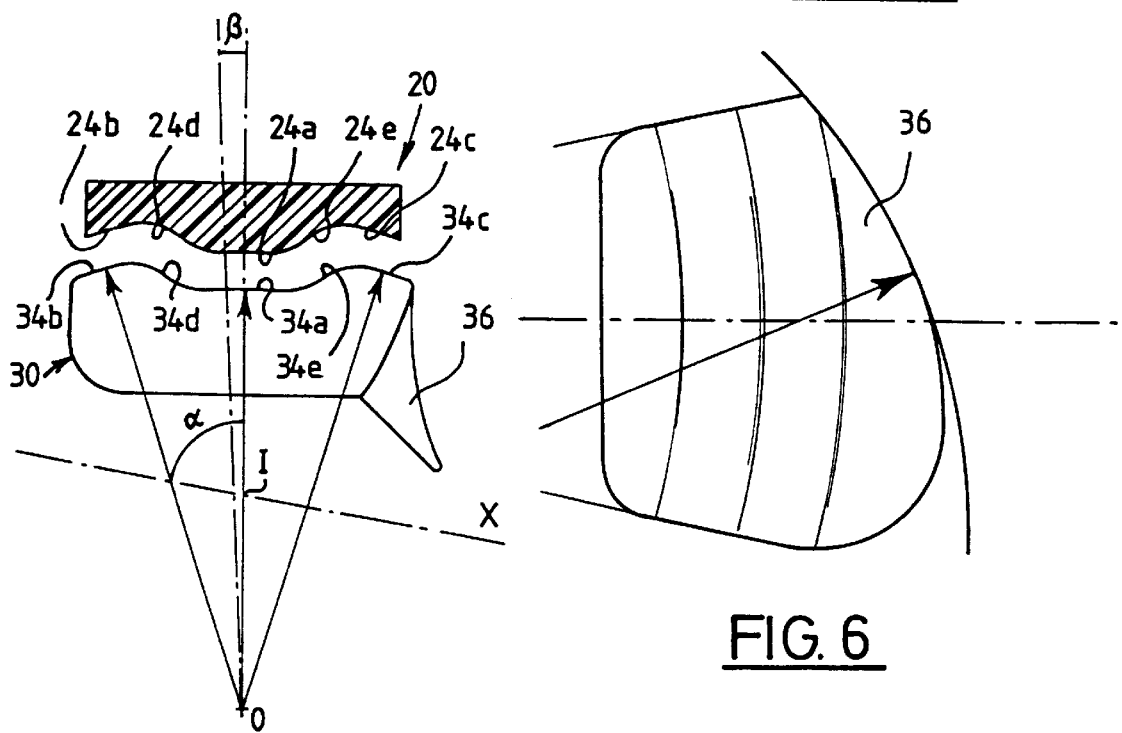
FIG. 5
FIG. 6

ANKLE PROSTHESIS

BACKGROUND OF THE INVENTION

1. Field of the Invention

The present invention relates to ankle prostheses.

2. Brief Description of the Related Art

Numerous prostheses were put forth that comprise a tibial and a talar element, each provided with an articular surface; these articular surfaces are shaped in such a manner that, by interacting as a whole, they provide the necessary articulation between the foot and the leg. Several shapes of articular surfaces were contemplated, some of which were spherical while others were constituted by surfaces of revolution around an axis essentially perpendicular to the tibial axis, allowing a rotary motion only around this one axis. Furthermore, one or the other of the tibial and talar elements can be provided with a plane interface, which allows a sliding between two elements, one of which is secured to the bone while the other one delimits the articular surface.

It must be noted, however, that in all the various currently used prostheses the obtained movement of the articulation does not correspond to the natural articular movement of the ankle, a fact that manifests itself in an inadequacy between the movement allowed by the articular surfaces and the movement the various ligaments tend to impose upon the foot. This inadequacy is evidenced by the appearance of limitations and stresses on the prosthesis which, in turn, can give rise to wear and tear, a loss of mobility or even a loosening of the prosthesis. Furthermore, it can cause discomfort and unpleasant pains to the patient.

SUMMMARY OF THE INVENTION

Thus, the object of the present invention is to present an ankle prosthesis that allows an improvement of this situation and to obtain an ankle kinematics that comes very close to that of a regular ankle.

To this effect, the object of the present invention is an ankle prosthesis, comprising a tibial element and an talar element, each one provided with anchoring means at the lower extremity of the tibia and at the astragalus, respectively, and each delimiting an articular surface; these two articular surfaces are shaped in such a manner as to interact as a whole and to provide a relative movement between the tibial and the talar elements around at least one axis, characterized by the fact that, taking as reference direction the orientation of the axis of the tibia at which the tibial element is to be anchored, when seen in projection on a plane that is essentially perpendicular to this reference direction, the articular surfaces are curved with a concavity oriented toward the inside of the foot on which the talar element is to be anchored.

In accordance with other characteristics

- each of the articular surfaces is provided with a central bearing surface and two lateral abutting surfaces, with play between the lateral abutting surfaces of the two articular surfaces, allowing a limited lateral deflection between these two articular surfaces;
- the play between the lateral abutting surfaces varies according to the length of the articular surfaces;
- the play between the lateral abutting surfaces is grater in the back of the prosthesis than in its front;
- the play between the lateral abutting surfaces corresponds to an angular deflection of less than 5° on both sides of a medial position;
- each of the articular surfaces is provided with a central surface and two lateral bearing surfaces; these two latter are at different levels than that of the central bearing surface, being the lateral abutting surfaces formed by connecting areas between the central and the lateral bearing surfaces;
- each articular surface can be defined as being produced by the rotating of a plane directrix line, comprising at least one circular arc, around at least one axis in its plane and running in an oblique direction with respect to the mean or median radius of said circular arc;
- the axis around which the directrix is rotated, being the directrix supposedly located on an essentially vertical plane, is directed towards the inside and upwards with respect to the mean or median radius of this directrix;
- the directrix is formed by three circular arcs, one central and two lateral arcs, connected by two curves, each of which includes a point of inflection;
- the talar element of the prosthesis comprises a lateral S-curved articular surface, which curvatures are convex in a front-to-back direction and concave in a vertical direction, adapted to interact with the area adjacent to the lower extremity of the fibula.

BRIEF DESCRIPTION OF THE DRAWINGS

The present invention is described below in more details, making reference to the accompanying drawings given only by way of example and in which:

FIGS. 2 to 4 are top, side elevation and bottom views, respectively, of the talar element;

FIG. 5 is a diagrammatic representation detailing the profile and the manner of generating the articular surfaces, and FIG. 6 is a diagrammatic plan view of a variant.

FIG. 1 shows the lower extremities of a tibia T and of a fibula P as well as the astragalus A located in the proximity of the extremities of these two bones.

DESCRIPTION OF THE PREFERRED EMBODIMENT

Figure 1:
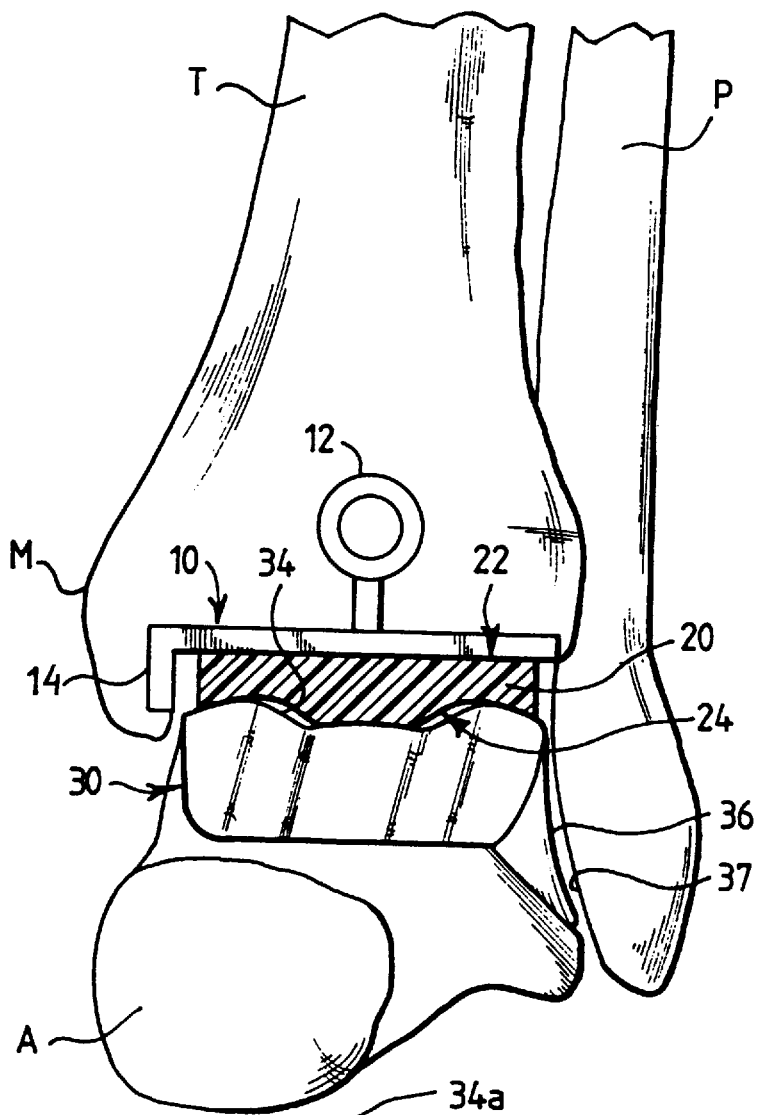
FIG. 1 shows a partially cutaway front view of a prosthesis, in accordance with the present invention, for a left foot.

The prosthesis in accordance with the present invention comprises a plate 10 anchored at the lower extremity of the tibia, being this extremity suitably prepared. In the shown example, the tibial plate 10 is anchored in the bone by means of a hollow anchoring rod 12, but any other suitable anchoring device can be used. This plate is provided with a flange 14 on the side facing the internal malleolus M. This plate can be made out of any biocompatible material, such as: chromium steel, titanium, ceramic or others.

A pad 20 made out of a material having a low friction coefficient such as, for example, high-density polyethylene, is provided with a plane surface 22 resting against the plate 10, and is delimited on its side opposite to an articular surface 24. In order to limit the deflections between the plate 10 and the pad 20, the plate may be provided with a pin lodged in a recess in the plane side of the pad; the dimensions of this housing determine the course of the admissible relative movement between the two elements. These means, known in the discipline, are not illustrated.

The assembly constituted by the plate 10 and the pad 20 constitutes the tibial element of the prosthesis.

The talar element is constituted by a block 30 out of chromium steel, titanium or ceramic, by way of example, affixed at the upper portion of the astragalus by a hollow stud 32 and a rib 33 or by another suitable means, and delimiting an upper articular surface 34 intended to interact with the combined articular surface 24 delimited by the pad 20.

In accordance with the present invention, and as illustrated in the drawings (FIGS. 1 and 5), the talar articular surface is provided with a central bearing surface 34a with a frontal and sagittal S curve. Also provided are two other lateral bearing surfaces 34b, 34c that present the same S curve. The two lateral bearing surfaces are not positioned at the same level as the central surface and the connecting zones 34d and 34e between the central zone and the lateral zones constitute the abutting surfaces for the combined articular tibial surface.

In the illustrated embodiment (FIG. 5), the articular talar surface 34 is created by a directrix curve inside of a plane and consists of a central section an d two lateral sections formed by concentric circular arcs, connected by curve sections presenting a point of inflection. These various sections of the directrix are designated by the same references 34a to 34e as the corresponding surfaces. By way of example, the radii of the central section 34a and of the lateral sections 34b, 34c can be of approximately 35 mm and 40 mm, respectively.

To create the entire articular talar surface, one makes the directrix rotate around an axis X that is contained in the plane of this directrix and running in an oblique direction with respect to the mean or median radius of the central section 34a. Preferably, the angle $\alpha$ formed by this axis with the median radius is comprised between 70 and 85° and the distance between the point I of intersection of this axis with the median radius and the central section of the directrix is roughly 10 to 24 mm.

Figure 2:
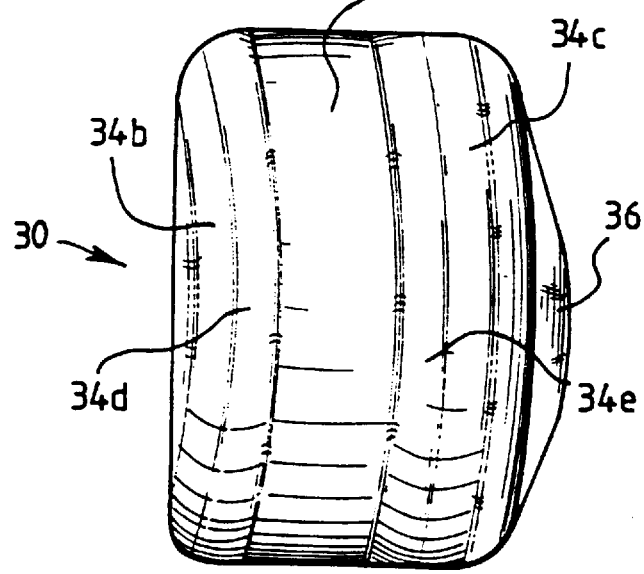

This manner of generating the articular surface is shown by the fact that in a plan or projection view on a plane essentially perpendicular to the axis of the tibia (FIG. 2), the articular surface has a curved shape, with its concavity towards the internal malleolus M or towards the inside of the foot of a patient susceptible to wear such a prosthesis.

The piece 30 is further provided with a lateral section 36 delimiting an articular surface interacting with the adjacent section 37 of the lower extremity of the fibula. In accordance with an important feature, this surface is convex in a front-to-back direction and concave in the vertical direction. In a projection view on a plane approximately horizontal or perpendicular to the axis of the tibia, it can be more or less concentric to the articular surface 34 (FIG. 2) or, on the contrary, be centered on a point shifted forward with respect to the center of the curvature of the surface 34 (FIG. 6).

The articular tibial surface 24 delimited by the lower side of the pad 20 has a profile analogous to that of the articular talar surface, with complementary shapes, that is to say, concave when the articular talar surface is convex. Thus, on this articular surface can be found a central section 24a and lateral bearing surfaces 24b, 24c that interact with the corresponding sections of the other articular surface; the central section 24a, however, is not as large as the other central section 34a, in order to bring about a lateral play determined between the abutting surfaces 24d, 24e, 34d, 34e, constituted by the connecting or transition areas between the central and the lateral bearing surfaces.

This lateral play allows, for example, on both sides of a mid-position an angular displacement of $\pm\beta$ of $\pm 2°$ around the instantaneous center of rotation constituted by the center O of said bearing surfaces. The angle $\beta$ can be comprised between 0 and 5°.

Such a prosthesis offers a kinematics that is very close to that of the natural ankle articulation, thus assuring a good adequation between the articulation movement afforded by the articular surfaces and the forces exerted by the ligaments. Furthermore, for the various positions of the ankle there is obtained a good congruence between the articular surfaces and a very favorable positioning of the instantaneous centers of rotation.

It can be added that in the cases where an ankle prosthesis is contemplated, one uses frequently the calcaneum which causes in the patient a blocking of movement between the heel and the astragalus. The prosthesis in accordance with the present invention, because of the limited lateral play that is provided, compensates this disadvantage to a great extent.

As a variant, for this lateral angular play, the back of the articulation can be given a greater value than its front section. Thus, this angular play that is of $\pm 2°$ in the front area can increase up to $\pm 4°$ or 5° in the back.

Furthermore, many variants can be used for this prosthesis, that especially apply to the methods of anchoring to the tibia and the astragalus, as well as to the shape and the manufacture of the constituent elements of the prosthesis.

To the extent where the articular surfaces present the desired curvature, with a concavity towards the inside, they can be produced according to profiles other than the one illustrated. For example, in a first section extending from the back extremity up to two thirds or three fourths of the length of the articular surfaces, these articular surfaces can be created as described above by a rotation of the directrix around the axis X, while in the rest of the front section, the surface can be created by rotation of the same directrix around a second axis closer to the directrix and parallel or not to the axis X. In such a case, the curvature, in projection on a more or less horizontal plane, is larger in its front than in the back section of the articular surfaces. The position and the inclination of this second axis are thus chosen in a manner that allows the obtaining of the desired curvature and an appropriate transition with the first section of the surface.

What we claim is:

1. An ankle prostheses comprising; a
tibial element having an inner side adapted to be positioned toward the inside of a foot and an outer portion adapted to be oriented toward a lower portion of an outer fibula and a talar element having an inner side adapted to be positioned toward the inside of a foot and an outer portion adapted to be positioned toward the lower portion of the outer fibula, said tibial element including means for anchoring to a tibia and said talar element including means for anchoring to an astragalus, said tibial element including a lower articular surface which cooperatively engages an upper articular surface of said talar element, and each of said lower articular surface and upper articular surface being concavely curved toward the inside of a foot and thus toward said inner sides of said tibial element and said talar element, respectively, from a front of each of said tibial element and said talar element to a rear of said tibial element and said talar element.

2. The ankle prosthesis of claim 1 wherein said articular surface of said tibial element includes a central bearing surface having two outer lateral abutting surfaces on opposite sides thereof, and said articular surface of said talar element includes a central bearing surface engageable with said central bearing surface of said tibial element and having two outer lateral abutting surfaces on opposite sides thereof which are engageable with said two outer lateral abutting surfaces of said tibial element.

3. The ankle prosthesis of claim 2 wherein said two outer lateral abutting surfaces of said talar element extend upwardly relative to said central bearing surface thereof between said front and rear of said talar element, and said central bearing surface of said tibial element extends below said two outer lateral abutting surfaces thereof from said front to said rear of said tibial element.

4. The ankle prosthesis of claim 3 wherein said central bearing surfaces of said tibial element and said talar element are of different dimension when measured between said two outer lateral abutting surfaces thereof to thereby form a lateral clearance between opposing of said two outer lateral abutting surfaces of each of said articular surfaces.

5. The ankle prosthesis of claim 4 wherein said lateral clearance varies from adjacent said front of said tibial element and said talar element to said rear of said tibial element and said talar element.

6. The ankle prosthesis of claim 2 wherein each of said articular surfaces of said tibial element and said talar element further includes two outer bearing surfaces connected to said central bearing surfaces by said lateral abutting surfaces.

7. The ankle prosthesis of 4 claim wherein said bearing lateral clearance between said lateral abutting surfaces is equal to an annular deflection $\beta$ of less than 5° on both sides of a mid-position between said central bearing surfaces of each of said articular surfaces.

8. The ankle prosthesis of claim 1 wherein each of said articular surfaces includes a central bearing surface which is connected to lateral bearing surfaces on opposite sides thereof by lateral abutting surfaces.

9. The ankle prosthesis of claim 1 wherein in each of said articular surfaces is defined by rotation of a directrix line having at least one circular arc around at least one axis "X" in its plane and extending in an oblique direction with respect to a median radius of said at least one circular arc.

10. The ankle prosthesis of claim 9 wherein the axis "X" is located in a vertical plane directed towards said inner side of said talar element and upward with respect to said median radius.

11. The ankle prosthesis of claim 10 wherein said axis "X" forms an angle of between 70° and 85° with said median radius of said directrix.

12. The ankle prosthesis of claim 9 wherein the distance between a point of intersection of the axis X of the articular surfaces with a median radius of said surface and a central portion of said central bearing surface of said talar element is between 10 and 24 mm.

13. The ankle prosthesis of claim 1 wherein said curvature of said articular surfaces is greater adjacent said front of said tibial element and said talar element than adjacent said rears thereof.

14. The ankle prosthesis of claim 1 wherein said outer portion of said talar element is generally convex in configuration between said front toward said rear thereof and is concave in a vertical direction from a lower portion to an upper portion thereof.

15. The ankle prosthesis of claim 5 wherein said lateral clearance increases from adjacent said front of said tibial element and said talar element to said rear of said tibial element and said talar element.

* * * * *